(12) United States Patent
Kono

(10) Patent No.: US 11,033,173 B2
(45) Date of Patent: Jun. 15, 2021

(54) MEDICAL LIGHT SOURCE DEVICE AND MEDICAL OBSERVATION SYSTEM

(71) Applicant: Sony Olympus Medical Solutions Inc., Tokyo (JP)

(72) Inventor: Hidetaro Kono, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 16/729,525

(22) Filed: Dec. 30, 2019

(65) Prior Publication Data
US 2020/0297184 A1 Sep. 24, 2020

(30) Foreign Application Priority Data
Mar. 19, 2019 (JP) .............................. JP2019-051415

(51) Int. Cl.
*A01B 1/00* (2006.01)
*A61B 1/00* (2006.01)
*A61B 1/06* (2006.01)
*H04N 5/378* (2011.01)
*H04N 5/353* (2011.01)

(52) U.S. Cl.
CPC ............ *A61B 1/00006* (2013.01); *A61B 1/06* (2013.01); *H04N 5/3532* (2013.01); *H04N 5/378* (2013.01)

(58) Field of Classification Search
CPC .. H04N 5/3532; H04N 5/378; A61B 1/00006; A61B 1/06
USPC ........................................................... 348/68
See application file for complete search history.

(56) References Cited

U.S. PATENT DOCUMENTS

| 10,025,087 B2* | 7/2018 | Mori | A61B 1/00172 |
| 2007/0225560 A1* | 9/2007 | Avni | A61B 1/0684 600/118 |
| 2008/0287742 A1* | 11/2008 | St. George | A61B 1/00009 600/160 |
| 2013/0193875 A1* | 8/2013 | Godo | A61B 1/00006 315/297 |
| 2014/0371535 A1* | 12/2014 | Seto | A61B 1/0661 600/160 |
| 2017/0168286 A1* | 6/2017 | Mori | G02B 23/2484 |

FOREIGN PATENT DOCUMENTS

WO 2013/157368 A1 10/2013

* cited by examiner

*Primary Examiner* — Joseph G Ustaris
*Assistant Examiner* — Jimmy S Lee
(74) *Attorney, Agent, or Firm* — Xsensus LLP

(57) ABSTRACT

A medical light source device includes: a light emitting element; and a processor comprising hardware. The processor is configured to: determine a light source control value; and control the light emitting element to emit light with a light emission amount according to the light source control value by controlling at least one of a supply time of a current and a current value that are supplied to the light emitting element. The processor is further configured to: turn off the light emitting element in the readout period, when the light source control value decreases from a first value to a second value; and turn on the light emitting element in the readout period, when the light source control value increases from a third value, different from the second value, to a fourth value.

5 Claims, 7 Drawing Sheets

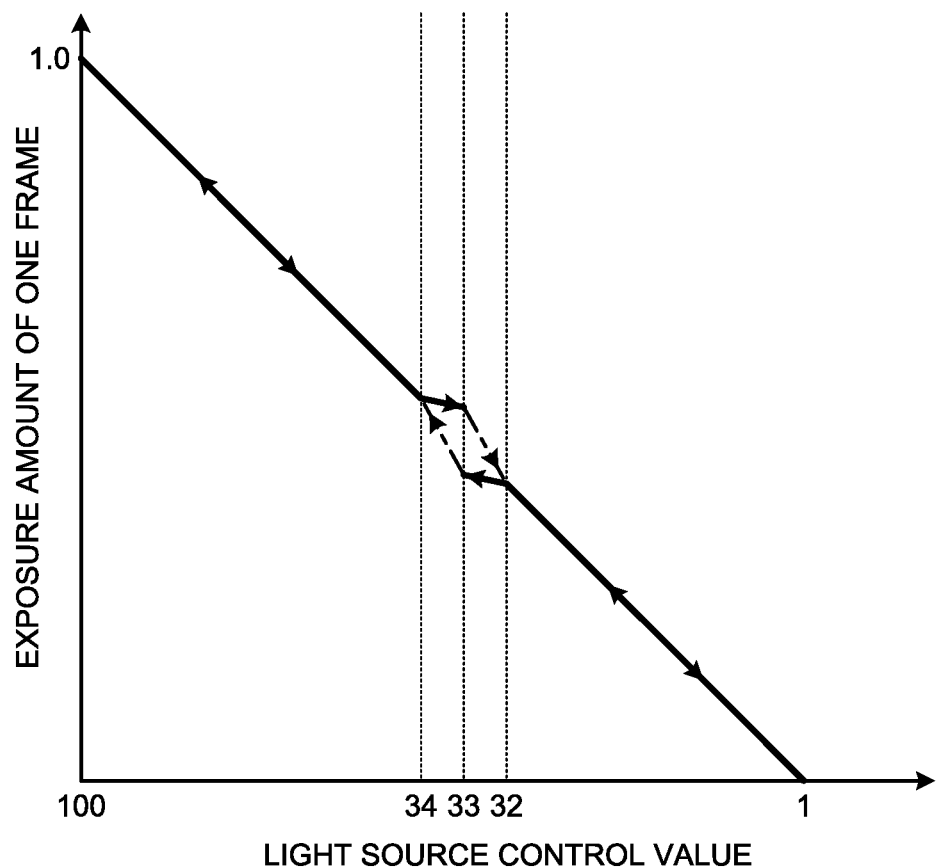

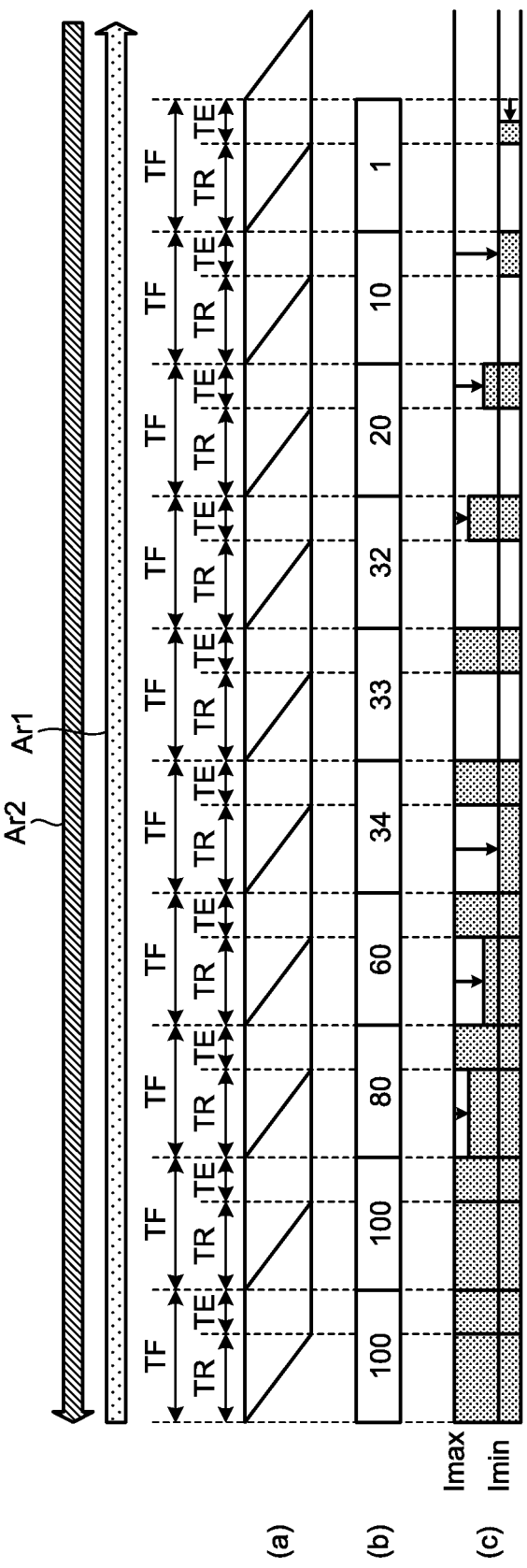

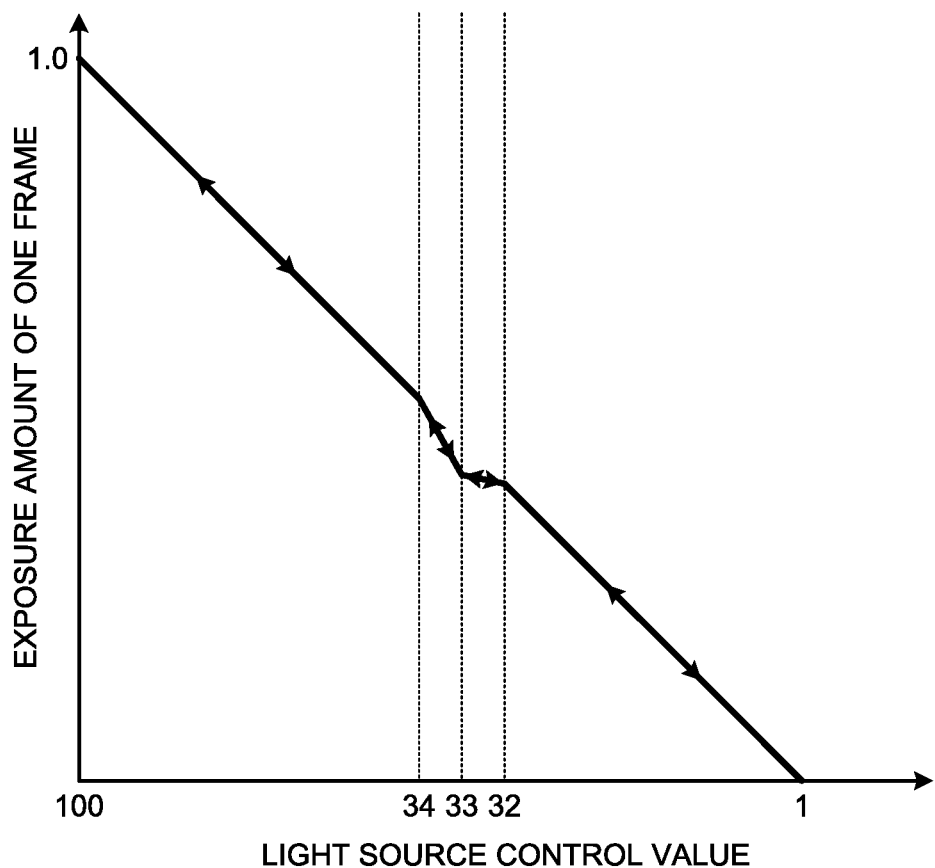

MEDICAL LIGHT SOURCE DEVICE AND MEDICAL OBSERVATION SYSTEM

This application claims priority from Japanese Application No. 2019-051415, filed on Mar. 19, 2019, the contents of which are incorporated by reference herein in its entirety.

BACKGROUND

The present disclosure relates to a medical light source device and a medical observation system.

In the related art, there is known a medical observation system that captures a subject (inside of a living body) by using a CMOS (Complementary Metal Oxide Semiconductor), a rolling shutter type image sensor, so that the inside of the living body is observed (see, for example, International Publication No. 2013/157368).

In the medical observation system described in International Publication No. 2013/157368, the following configuration is adopted as a medical light source device that supplies illumination light to be emitted into the inside of a living body.

The medical light source device includes: a light emitting element that emits light according to a supplied current; and a control unit that causes the light emitting element to emit light with a light emission amount according to a light source control value by controlling at least one of an applied pulse width of a current (current supply time) and a current value that are supplied to the light emitting element. The light source control value is a value indicating a target value of the light emission amount of the light emitting element in one frame period TF (see FIG. 6) composed of an entire line exposure period TE (see FIG. 6) in which all horizontal lines of the CMOS are exposed simultaneously and a readout period TR (see FIG. 6) for the CMOS.

FIG. 6 is a diagram for explaining dimming control in the related art. Specifically, (a) of FIG. 6 is a diagram illustrating the exposure timing of the CMOS, where the vertical axis represents the horizontal lines of the CMOS (the topmost line indicates the highest horizontal line (first horizontal line) and the bottom line indicates the lowest horizontal line (final line)), and the horizontal axis represents time. (b) of FIG. 6 illustrates light source control values. In (b) of FIG. 6, the minimum value of the light source control value is set to "1", and the maximum value to "100." (c) of FIG. 6 is a diagram illustrating dimming control by the control unit, where the vertical axis represents a current value supplied to the light emitting element, and the horizontal axis represents the applied pulse width of a current (current supply time) supplied to the light emitting element. In the following, for convenience of explanation, the current value supplied to a light emitting element is described only as a "current value", and the applied pulse width of a current supplied to the light emitting element is described only as "supply time." FIG. 6 illustrates both of dimming control (hereinafter referred to as first dimming control) when the light source control value decreases (when the light emission amount of the light emitting element is reduced (arrow Ar1 in FIG. 6)), and dimming control (hereinafter referred to as second dimming control) when the light source control value increases (when the light emission amount of the light emitting element is increased (arrow Ar2 in FIG. 6)).

The control unit, which constitutes the medical light source device described in International Publication No. 2013/157368, executes, for example, dimming control as described below.

First, the first dimming control when the light source control value decreases will be described.

When the light source control value is the maximum value "100", the control unit sets the current value as a maximum rated current value Imax in the entire period of the readout period TR and in the entire period of the entire line exposure period TE, in the one frame period TF.

When the light source control value decreases from the maximum value "100", the control unit reduces the current value in the entire period of the readout period TR, while maintaining the current value in the entire period of the entire line exposure period TE at the maximum rated current value Imax. When the light source control value reaches "34", the control unit sets the current value in the entire period of the readout period TR as a minimum rated current value Imin.

When the light source control value further decreases from "34" to "33", the control unit turns off a light emitting element 31 in the entire period of the readout period TR, while maintaining the current value in the entire period of the entire line exposure period TE at the maximum rated current value Imax.

When the light source control value further decreases from "33", the control unit reduces the current value in the entire period of the entire line exposure period TE from the maximum rated current value Imax, while maintaining the state where the light emitting element is turned off in the entire period of the readout period TR. When the light source control value reaches "10", the control unit sets the current value in the entire period of the entire line exposure period TE as the minimum rated current value Imin.

When the light source control value further decreases from "10" to the minimum value "1", the control unit reduces the supply time in the entire line exposure period TE by PWM control, while maintaining the state where the light emitting element is turned off in the entire period of the readout period TR, and maintaining the current value in the entire line exposure period TE at the minimum rated current value Imin.

When the light source control value increases, the control unit executes the same control (second dimming control) as the first dimming control for each light source control value.

FIG. 7 is a graph showing a relationship between an exposure amount of one frame and a light source control value in the related art.

In the dimming control, a curve indicating a relationship between an exposure amount of one frame and a light source control value in the first dimming control (a curve with an arrow pointing to a direction in which the light source control value decreases), and a curve indicating a relationship between an exposure amount of one frame and a light source control value in the second dimming control (a curve with an arrow pointing to a direction in which the light source control value increases) have the same route, as illustrated in FIG. 7.

In the dimming control described above, the supply time is not changed by PWM control in the readout period TR, and hence wide dynamic range dimming is achieved, while uneven exposure within one frame is being suppressed.

SUMMARY

In the first dimming control, the light emission amount of the light emitting element in the readout period TR decreases by a relatively large amount of light, even when the light emitting element is turned off when the current value is the minimum rated current value Imin. Similarly, in the second dimming control, the light emission amount of the light emitting element in the readout period TR increases by a relatively large amount of light, even when the light emitting element is turned on, at a current value of the minimum rated current value Imin, from the state where the light emitting element is turned off. And, as a result of the change in the amount of light accompanying a change in which the light emitting element is turned from on to off or from off to on, "brightness discontinuity between frames", "uneven exposure within one frame", etc., are concerned as the influences on the image quality.

In particular, in the above-described dimming control, both the first and second dimming controls allow the light emitting element to be turned from on to off or from off to on at the same point (between "34" and "33" of the light source control value). Therefore, when a dimming target is around the point, there is a possibility that the light emitting element may be repeatedly turned from on to off and from off to on, and there is a risk that the above influences on the image quality may be at a level where user observation is disturbed.

So, there is a demand for a technique that enables an image suitable for observation to be generated.

There is a need for a medical light source device and a medical observation system that generate an image suitable for observation.

According to one aspect of the present disclosure, there is provided a medical light source device including: a light emitting element configured to emit light according to a supplied current; and a processor including hardware, the processor being configured to: determine a light source control value indicating a target value of a light emission amount of the light emitting element in one frame period including both an exposure period, in which all horizontal lines of a rolling shutter type image sensor in which a plurality of pixels are arranged two-dimensionally in units of the horizontal lines are simultaneously exposed, and a readout period for charges accumulated in the plurality of pixels; and control the light emitting element to emit light with a light emission amount according to the light source control value by controlling at least one of a supply time of a current and a current value that are supplied to the light emitting element, wherein the processor is further configured to: turn off the light emitting element in the readout period, when the light source control value decreases from a first value to a second value in a state where the light emitting element is turned on in the readout period; and turn on the light emitting element in the readout period, when the light source control value increases from a third value, different from the second value, to a fourth value in a state where the light emitting element is turned off in the readout period.

BRIEF DESCRIPTION OF THE DRAWINGS

FIG. 5 is a graph showing a relationship between an exposure amount of one frame and a light source control value;

FIG. 6 is a diagram for explaining dimming control; and

FIG. 7 is a graph showing a relationship between an exposure amount of one frame and a light source control value.

DETAILED DESCRIPTION

Figure 1:
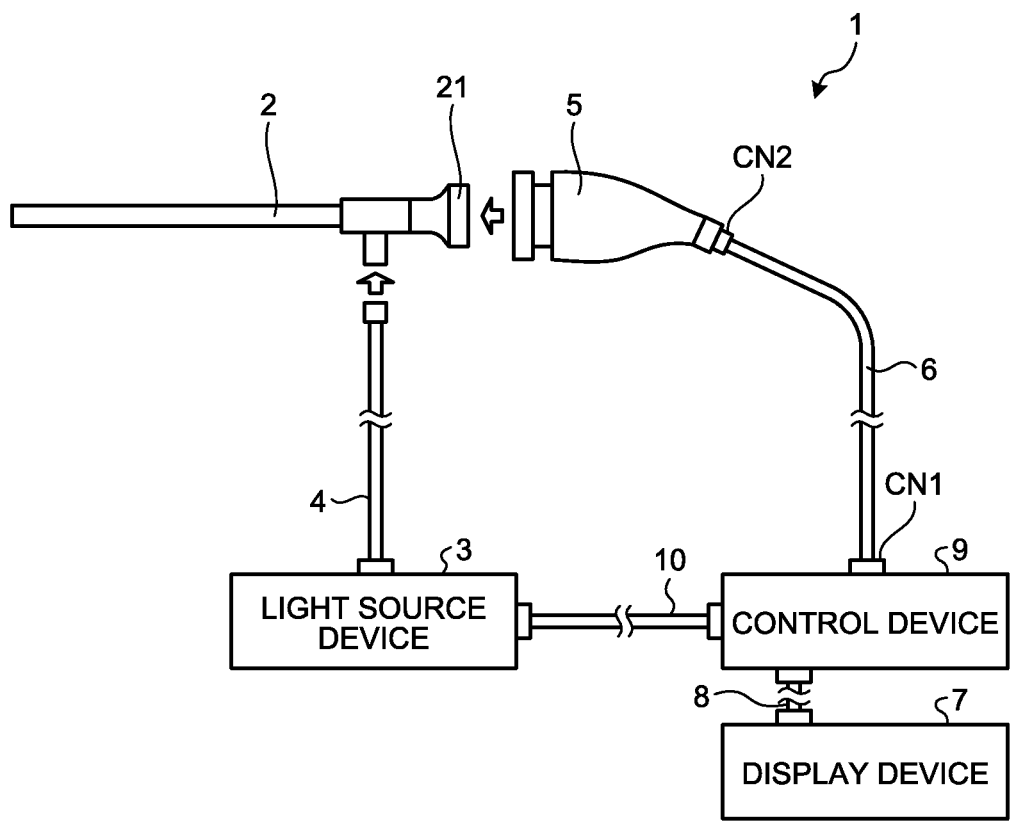
FIG. 1 is a diagram illustrating a configuration of a medical observation system according to an embodiment.

Hereinafter, forms for carrying out the present disclosure (hereinafter referred to as embodiments) will be described with reference to the drawings. The present disclosure is not limited by the embodiments described below. In description of the drawings, the same portions are denoted by the same reference numerals.

Schematic Configuration of Medical Observation System

FIG. 1 is a diagram illustrating a configuration of a medical observation system 1 according to the present embodiment.

The medical observation system 1 is a system that is used in a medical field to capture (observe) a living body (observation target) that is a subject. As illustrated in FIG. 1, the medical observation system 1 includes an insertion portion 2, a light source device 3, a light guide 4, a camera head 5, a first transmission cable 6, a display device 7, and a second transmission cable 8, a control device 9, and a third transmission cable 10.

In the present embodiment, the insertion portion 2 is configured with a rigid endoscope. That is, the insertion portion 2 has an elongated shape, the entire of which is rigid or part of which is flexible and the other parts are rigid, and is inserted into the inside of a living body. An optical system is provided in the insertion portion 2, the optical system being configured by using one or more lenses to collect light from a subject.

The light source device 3 is connected to one end of the light guide 4 in order to supply light for illuminating the inside of a living body to the one end of the light guide 4 under control by the control device 9. The light source device 3 includes the light emitting element 31 and a drive unit 32 (see FIG. 2).

The light emitting element 31 emits light according to the supplied current. The light from the light emitting element 31 is supplied to the one end of the light guide 4 as light for illuminating the inside of a living body. Examples of the light emitting element 31 include an LED (Light Emitting Diode) that emits white light, etc. The light from the light emitting element 31 is not limited to white light, and may be light in other wavelength bands. Also, the light emitting element 31 is not limited to an LED, and may be configured with a semiconductor laser, etc.

The drive unit 32 drives the light emitting element 31 by supplying current to the light emitting element 31 under the control by the control device 9. More specifically, the drive unit 32 may adjust an amount of light emitted by the light emitting element 31, by changing the current value to be supplied to the light emitting element 31 or the applied pulse width of a current (current supply time) to be supplied to the light emitting element 31.

In the present embodiment, the light source device 3 is configured separately from the control device 9, but without being limited thereto, a configuration may be adopted, in which the light source device 3 is provided in the control device 9.

One end of the light guide 4 is detachably connected to the light source device 3, and the other end is detachably connected to the insertion portion 2. The light guide 4 transmits the light supplied from the light source device 3 from the one end to the other end, so that the light is supplied to the insertion portion 2. The light supplied to the insertion portion 2 is emitted from the end of the insertion portion 2 to be emitted into the inside of a living body. The light (subject image), emitted into the inside of a living body and reflected in the inside of the living body, is collected by the optical system in the insertion portion 2.

The camera head 5 corresponds to an imaging device according to the present disclosure. The camera head 5 is detachably connected to the proximal end (an eyepiece 21 (FIG. 1)) of the insertion portion 2. The camera head 5 captures a subject image collected in the insertion portion 2 under the control by the control device 9, and outputs an image signal (RAW signal) by the capturing. The image signal is, for example, an image signal of 4K or higher.

The detailed configuration of the camera head 5 will be described later.

The first transmission cable 6 has one end detachably connected to the control device 9 via a connector CN1 (FIG. 1) and the other end detachably connected to the camera head 5 via a connector CN2 (FIG. 1). The first transmission cable 6 transmits an image signal, etc., output from the camera head 5 to the control device 9, and transmits a control signal, a synchronization signal, a clock, power, etc., output from the control device 9 to the camera head 5, respectively.

The transmission of an image signal, etc., from the camera head 5 to the control device 9 via the first transmission cable 6 may be performed by transmitting the image signal, etc., as optical signals or as electrical signals. The same applies to the transmission of a control signal, a synchronization signal, and a clock from the control device 9 to the camera head 5 via the first transmission cable 6.

The display device 7 is configured with a display using liquid crystal, organic EL (Electro Luminescence), or the like, and displays an image based on a video signal from the control device 9 under the control by the control device 9.

The second transmission cable 8 has one end detachably connected to the display device 7 and the other end detachably connected to the control device 9. The second transmission cable 8 transmits a video signal processed by the control device 9 to the display device 7.

The control device 9 is configured with a CPU (Central Processing Unit), an FPGA (Field-Programmable Gate Array), or the like, to comprehensively control operations of the light source device 3, the camera head 5, and the display device 7.

The detailed configuration of the control device 9 will be described later.

The third transmission cable 10 has one end detachably connected to the light source device 3 and the other end detachably connected to the control device 9. The third transmission cable 10 transmits a control signal from the control device 9 to the light source device 3.

Configuration of Camera Head

Next, the configuration of the camera head 5 will be described.

Figure 2:
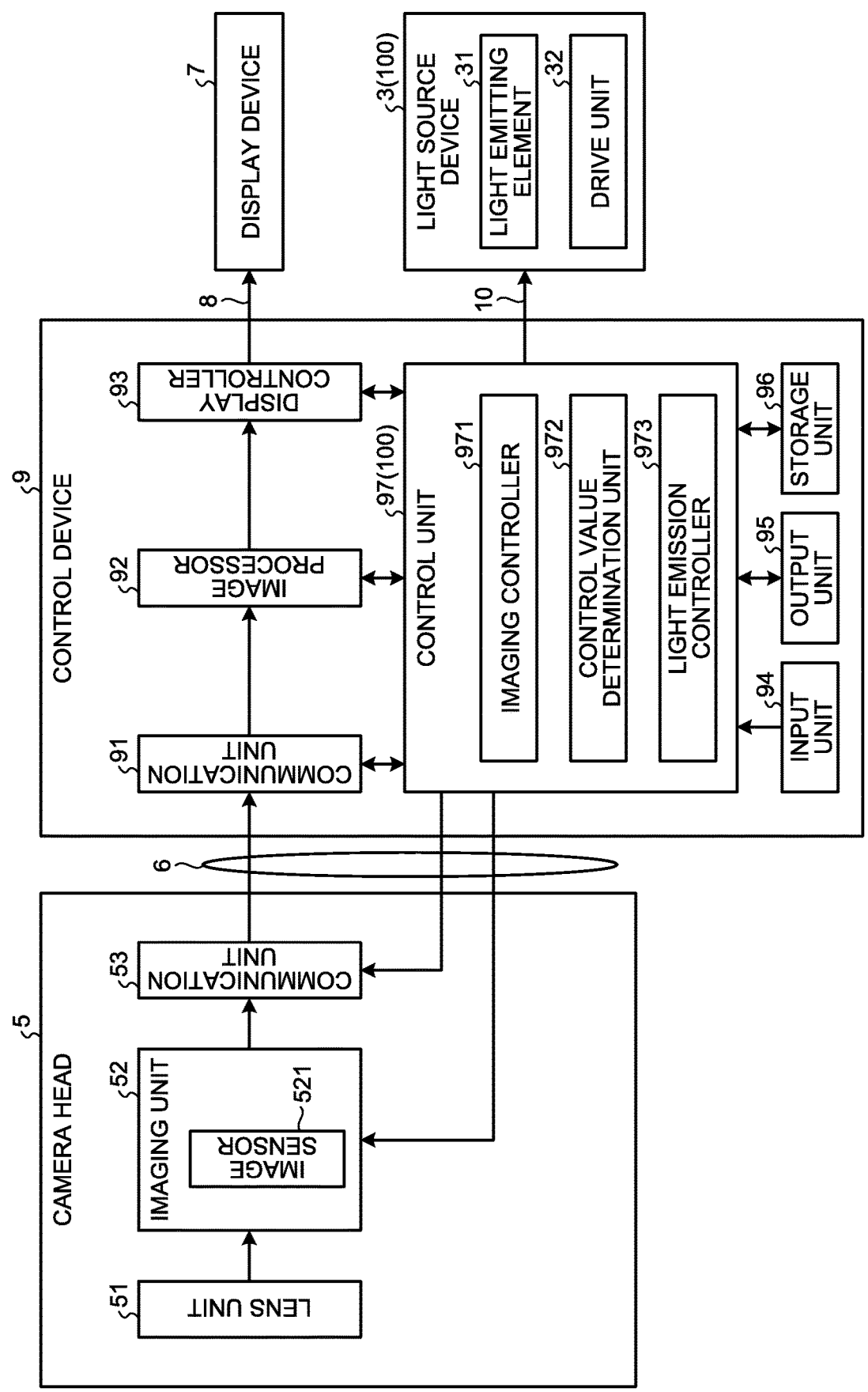
FIG. 2 is a block diagram illustrating configurations of a camera head and a control device.

FIG. 2 is a block diagram illustrating the configurations of the camera head 5 and the control device 9.

In FIG. 2, for convenience of explanation, the connectors CN1 and CN2 between the control device 9 and the first transmission cable 6 and between the camera head 5 and the first transmission cable 6, the connectors between the control device 9 and the second transmission cable 8 and between the display device 7 and the second transmission cable 8, and the connectors between the control device 9 and the third transmission cable 10 and between the light source device 3 and the third transmission cable 10, are not illustrated.

As illustrated in FIG. 2, the camera head 5 includes a lens unit 51, an imaging unit 52, and a communication unit 53.

The lens unit 51 is configured by using one or more lenses, and forms a subject image collected in the insertion portion 2 on an imaging surface of the imaging unit 52 (image sensor 521).

The imaging unit 52 captures the inside of a living body under the control by the control device 9. The imaging unit 52 is configured by using a sensor chip in which: the image sensor 521 (FIG. 2), which receives a subject image that is collected in the insertion portion 2 and formed by the lens unit 51 and converts it into an electrical signal; a signal processor (not illustrated) that outputs an image signal by performing signal processing (A/D conversion, etc.) on the electrical signal (analog signal) from the image sensor 521; and the like are integrally formed, so that an image signal (digital signal) after the A/D conversion is output. The above signal processor (not illustrated) may be formed separately from the image sensor 521, without being integrally formed.

In the present embodiment, the image sensor 521 is configured with a CMOS that is a rolling shutter type image sensor in which a plurality of pixels are arranged two-dimensionally in units of horizontal lines. Hereinafter, for convenience of explanation, the image sensor 521 is described as a CMOS 521.

The communication unit 53 functions as a transmitter that transmits an image signal (RAW signal (digital signal)) output from the imaging unit 52 to the control device 9 via the first transmission cable 6. The communication unit 53 is configured with, for example, a high-speed serial interface that performs image signal communication at a transmission rate of 1 Gbps or higher with the control device 9 via the first transmission cable 6.

Configuration of Control Device

Next, the configuration of the control device 9 will be described with reference to FIG. 2.

As illustrated in FIG. 2, the control device 9 includes a communication unit 91, an image processor 92, a display controller 93, an input unit 94, an output unit 95, a storage unit 96, and a control unit 97.

The communication unit 91 functions as a receiver that receives an image signal (RAW signal (digital signal)) output from the camera head 5 (communication unit 53) via the first transmission cable 6. The communication unit 91 is configured with, for example, a high-speed serial interface that performs image signal communication at a transmission rate of 1 Gbps or higher with the communication unit 53.

The image processor 92 executes image processing on the image signal (RAW signal (digital signal)) output from the camera head 5 (communication unit 53) and received by the communication unit 91, under the control by the control unit 97.

Examples of the image processing include optical black subtraction processing, white balance adjustment processing, demosaic processing, color correction matrix processing, gamma correction processing, YC processing for converting an RGB signal (image signal) into a luminance signal and a color difference signal (Y, $C_B/C_R$ signal), and, in addition to these, the following detection processing, etc.

The detection processing is one in which based on a Y signal (luminance signal) for each pixel in a predetermined region (hereinafter referred to as a detection region) in the entire captured image based on an image signal, an average luminance value in the detection region is calculated. Then, the image processor 92 outputs the detection information (average luminance value) obtained by the detection processing to the control unit 97.

The display controller 93 generates a video signal for display based on the image signal (Y, $C_B/C_R$ signal) processed by the image processor 92, under the control by the control unit 97. Then, the display controller 93 outputs the video signal to the display device 7 via the second transmission cable 8. Thereby, the display device 7 displays an image based on the video signal.

The input unit 94 is configured with an operation device such as a mouse, a keyboard, or a touch panel, to accept a user operation by a user such as a doctor. Then, the input unit 94 outputs an operation signal according to the user operation to the control unit 97.

The output unit 95 is configured with a speaker, a printer, or the like, to output various information.

The storage unit 96 stores a program to be executed by the control unit 97, information necessary for the processing by the control unit 97, and the like.

The control unit 97 is configured with, for example, a CPU, an FPGA, or the like, and outputs a control signal via the first to third transmission cables 6, 8, and 10, so that the operations of the light source device 3, the camera head 5, and the display device 7 are controlled and the overall operations of the control device 9 are controlled. As illustrated in FIG. 2, the control unit 97 includes an imaging controller 971, a control value determination unit 972, and a light emission controller 973. The light source device 3 and the control unit 97 correspond to a medical light source device 100 (FIG. 2) according to the present disclosure.

Figure 3:
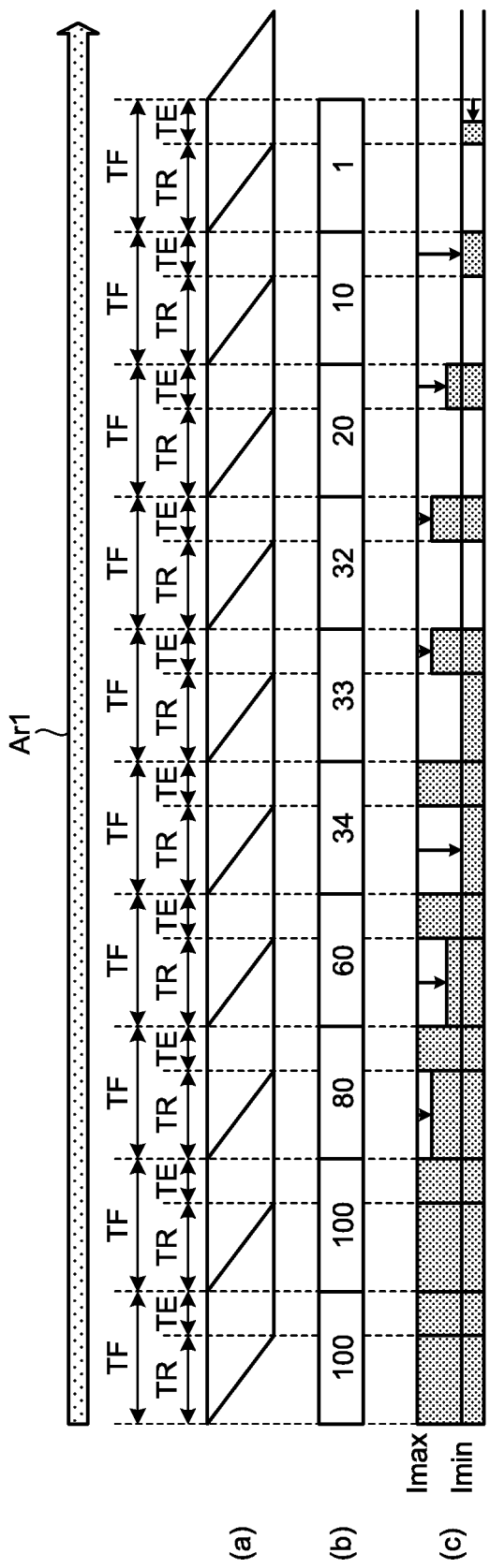
FIG. 3 is a diagram for explaining dimming control.
Figure 4:
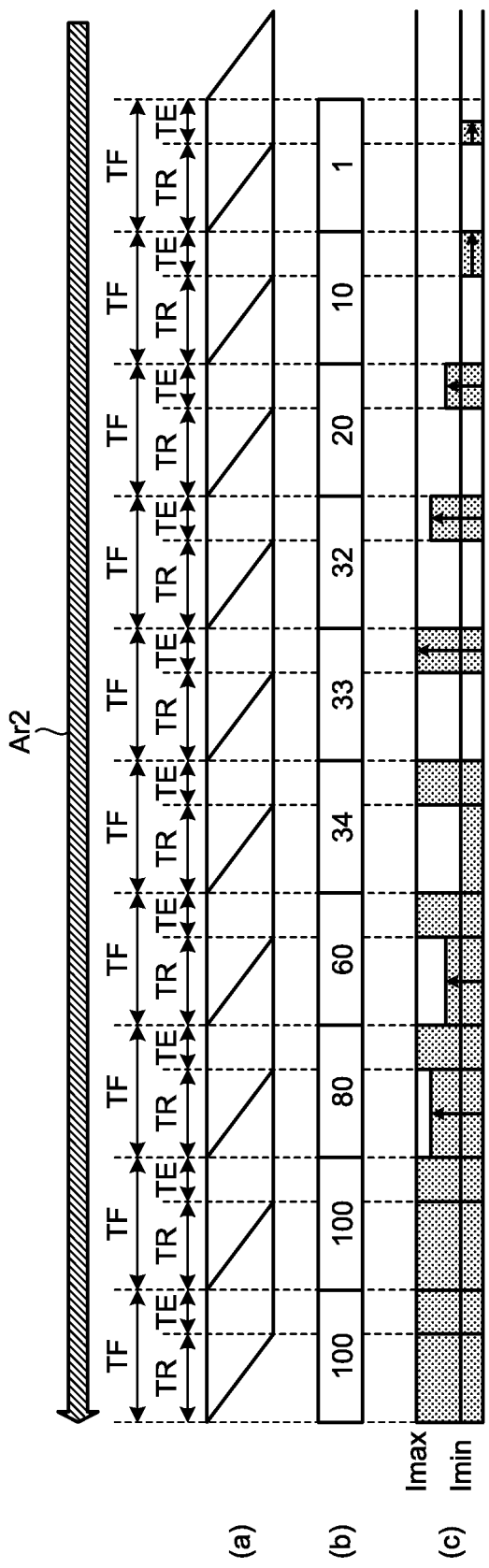
FIG. 4 is a diagram for explaining dimming control.

FIGS. 3 and 4 are diagrams for explaining dimming control. Specifically, (a) of FIG. 3 and (a) of FIG. 4 are diagrams illustrating the exposure timing of the CMOS 521, where the vertical axis represents the horizontal lines of the CMOS 521 (the topmost line indicates the highest horizontal line (first horizontal line) and the bottom line indicates the lowest horizontal line (final line)), and the horizontal axis represents time. (b) of FIG. 3 and (b) of FIG. 4 illustrate light source control values. In (b) of FIG. 3 and (b) of FIG. 4, the minimum value of the light source control value is set to "1", the maximum value to "100." (c) of FIG. 3 and (c) of FIG. 4 are diagrams illustrating dimming control by the light emission controller 973, where the vertical axis represents a current value to be supplied to the light emitting element 31, and the horizontal axis represents the applied pulse width of a current (current supply time) to be supplied to the light emitting element 31. In the following, for convenience of explanation, the current value to be supplied to the light emitting element 31 is described only as a "current value", and the applied pulse width of a current to be supplied to the light emitting element 31 is described only as "supply time." (c) of FIG. 3 illustrates dimming control (hereinafter referred to as first dimming control) when the light source control value decreases (when the light emission amount of the light emitting element 31 is reduced (arrow Ar1 in FIG. 3)). On the other hand, (c) of FIG. 4 illustrates dimming control (hereinafter referred to as second dimming control) when the light source control value increases (when the light emission amount of the light emitting element 31 is increased (arrow Ar2 in FIG. 4)).

The imaging controller 971 performs exposure control by a so-called rolling shutter system in which exposure in one frame period of the CMOS 521 is sequentially started for each horizontal line and reading is sequentially performed for each horizontal line after a predetermined period (so-called shutter speed) has elapsed from the start of exposure. In the present embodiment, the imaging controller 971 performs the exposure control such that as illustrated in (a) of FIG. 3 and (a) of FIG. 4, the one frame period TF is configured with an entire line exposure period TE in which all horizontal lines of the CMOS 521 are simultaneously exposed, and a readout period TR for charges accumulated in a plurality of pixels of the CMOS 521. Herein, the entire line exposure period TE corresponds to the exposure period according to the present disclosure.

Based on the detection information (average luminance value) output from the image processor 92, the control value determination unit 972 determines a light source control value for changing the brightness of a captured image obtained by imaging by the imaging unit 52 to a reference brightness (changing the average luminance value obtained by the detection processing to a reference average luminance value). The light source control value is one indicating the target value of the light emission amount of the light emitting element 31 in the one frame period TF.

The light emission controller 973 executes dimming control in which by controlling at least one of the current value and the supply time via the drive unit 32, the light emission controller 973 causes the light emitting element 31 to emit light with a light emission amount according to the light source control value determined by the control value determination unit 972.

Hereinafter, the first dimming control when the light source control value decreases and the second dimming control when the light source control value increases will be described in order.

First, the first dimming control will be described with reference to (c) of FIG. 3.

When the light source control value is the maximum value "100", the light emission controller 973 sets the current value as the maximum rated current value Imax in the entire period of the readout period TR and in the entire period of the entire line exposure period TE, in the one frame period TF.

When the light source control value decreases from the maximum value "100", the light emission controller 973 reduces the current value in the entire period of the readout period TR, while maintaining the current value in the entire period of the entire line exposure period TE at the maximum rated current value Imax. When the light source control value reaches "34", the light emission controller 973 sets the current value in the entire period of the readout period TR as the minimum rated current value Imin.

When the light source control value further decreases from "34" to "33", the light emission controller 973 reduces the current value in the entire period of the entire line exposure period TE from the maximum rated current value Imax, while maintaining the current value in the entire period of the readout period TR at the minimum rated current value Imin. That is, in the present embodiment, the light emission controller 973 starts reducing the current value in the entire period of the entire line exposure period TE from the maximum rated current value Imax, before turning off the light emitting elements 31 in the entire period of the readout period TR.

When the light source control value further decreases from "33" to "32", the light emission controller 973 turns off the light emitting element 31 in the entire period of the readout period TR, while maintaining the current value in the entire period of the entire line exposure period TE at a current value at which the light source control value is "33".

As described above, the light source control value "32" corresponds to a second value according to the present disclosure. The light source control value "33" corresponds to a first value according to the present disclosure.

When the light source control value further decreases from "32", the light emission controller 973 reduces the current value in the entire period of the entire line exposure period TE, while maintaining the state where the light emitting element 31 is turned off in the entire period of the readout period TR. When the light source control value reaches "10", the light emission controller 973 sets the current value in the entire period of the entire line exposure period TE as the minimum rated current value Imin.

When the light source control value further decreases from "10" to the minimum value "1", the light emission controller 973 reduces the supply time in the entire line exposure period TE by PWM control, while maintaining the state where the light emitting element 31 is turned off in the entire period of the readout period TR, and while maintaining the current value in the entire line exposure period TE at the minimum rated current value Imin.

Next, the second dimming control will be described with reference to (c) of FIG. 4.

When the light source control value increases from the minimum value "1" to "32", the light emission controller 973 executes the same control as the first dimming control for each light source control value, as may be seen by comparing (c) of FIG. 3 and (c) of FIG. 4.

When the light source control value further increases from "32" to "33", the light emission controller 973 sets the current value in the entire period of the entire line exposure period TE as the maximum rated current value Imax, while maintaining the state where the light emitting element 31 is turned off in the entire period of the readout period TR.

When the light source control value further increases from "33" to "34", the light emission controller 973 turns on the light emitting element 31 in the entire period of the readout period TR, while maintaining the current value in the entire period of the entire line exposure period TE at the maximum rated current value Imax. At this time, the light emission controller 973 turns on the light emitting element 31 at the minimum rated current value Imin. That is, in the present embodiment, the light emission controller 973 turns on the light emitting element 31 in the entire period of the readout period TR, after the current value in the entire period of the entire line exposure period TE reaches the maximum rated current value Imax.

As described above, the light source control value "34" corresponds to a fourth value according to the present disclosure. The light source control value "33" corresponds to a third value according to the present disclosure. That is, in the present embodiment, the light emission controller 973 turns off the light emitting element 31 in the readout period TR, when the light source control value decreases from the first value "33", smaller than the fourth value "34", to the second value "32" in the state where the light emitting element 31 is turned on in the readout period TR. Also, the light emission controller 973 turns on the light emitting element 31 in the readout period TR, when the light source control value increases from the third value "33", larger than the second value "32", to the fourth value "34" in the state where the light emitting element 31 is turned off in the readout period TR.

When the light source control value increases from "34" to the maximum value "100", the light emission controller 973 executes the same control as the first dimming control for each light source control value, as may be seen by comparing (c) of FIG. 3 and (c) of FIG. 4.

FIG. 5 is a graph showing a relationship between an exposure amount of one frame and a light source control value. Specifically, in FIG. 5, the curve with an arrow pointing to a direction in which the light source control value decreases corresponds to a curve indicating a relationship between an exposure amount of one frame and the light source control value in the first dimming control. On the other hand, the curve with an arrow pointing to a direction in which the light source control value increases corresponds to a curve indicating a relationship between an exposure amount of one frame and the light source control value in the second dimming control. In FIG. 5, the portions indicated by the dashed-dotted lines show a transition in which the light emitting element 31 is turned from on to off (hereinafter referred to as ON-OFF control) in the entire period of the readout period TR in the first dimming control, and a transition in which the light emitting element 31 is turned from off to on (hereinafter referred to as OFF-ON control) in the entire period of the readout period TR in the second dimming control.

The curve indicating the relationship between the exposure amount of one frame and the light source control value in the first dimming control, and the curve indicating the relationship between the exposure amount of one frame and the light source control value in the second dimming control have a so-called hysteresis relationship with each other, in which the light source control value has different paths between "34" and "32", as illustrated in FIG. 5. That is, as indicated by the dashed-dotted lines in FIG. 5, the ON-OFF control is executed at a point (hereinafter referred to as a first point) where the light source control value decreases from "33" to "32" in the first dimming control, while the OFF-ON control is executed at a point (hereinafter referred to as a second point) where the light source control value increases from "33" to "34" in the second dimming control.

According to the present embodiment described above, the following effects may be obtained.

In the medical light source device 100 according to the present embodiment, the first dimming control and the second dimming control execute the ON-OFF control and the OFF-ON control at different points (the first and second points), respectively.

Therefore, even when the dimming target is around the first point or around the second point, the possibility that the light emitting element 31 may be repeatedly turned from on to off or from off to on may be reduced. Therefore, influences on the image quality, such as "brightness discontinuity between frames" and "uneven exposure within one frame" due to changes in the light emission amount of the light emitting element 31 during the ON-OFF control and OFF-ON control, are prevented from being at a level where user observation is disturbed, whereby an image suitable for observation may be generated.

Other Embodiments

So far, an embodiment for carrying out the present disclosure has been described, but the present disclosure should not be limited by the embodiment described above.

In the above embodiment, the medical light source device 100 according to the present disclosure is mounted in the medical observation system 1 in which the insertion portion 2 is configured with a rigid endoscope; however, the present disclosure is not limited thereto. The medical light source device 100 according to the present disclosure may be mounted in a medical observation system in which the insertion portion 2 is configured with a flexible endoscope. Also, the medical light source device 100 according to the present disclosure may be mounted in medical observation systems such as a surgical microscope (see, for example, Japanese Laid-open Patent Publication No. 2016-42981) that magnifies and observes a predetermined field of view in a subject (the inside of a living body) or on the surface of a subject (the surface of a living body).

In the above embodiment, part of the configuration of the camera head 5 or part of the configuration of the control device 9 may be provided, for example, in the connector CN1 or the connector CN2.

In the above embodiment, when the light emission amount of the light emitting element 31 is changed in the entire line exposure period TE, the current value is changed when the light source control value is between "100" and "10" and the supply time is changed only when the light source control value is "1"; however, the present disclosure is not limited thereto. As long as at least one of the current value and the supply time is changed when the light emission amount of the light emitting element 31 is changed in the entire line exposure period TE, other configurations may be adopted.

According to the medical light source device and the medical observation system of the present disclosure, it is possible to generate an image suitable for observation.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical light source device comprising:
a light emitting element configured to emit light according to a supplied current; and
a processor comprising hardware, the processor being configured to:
determine a light source control value indicating a target value of a light emission amount of the light emitting element in one frame period including both an exposure period, in which all horizontal lines of a rolling shutter type image sensor in which a plurality of pixels are arranged two-dimensionally in units of the horizontal lines are simultaneously exposed, and a readout period for charges accumulated in the plurality of pixels; and
control the light emitting element to emit light with a light emission amount according to the light source control value by controlling at least one of a supply time of a current and a current value that are supplied to the light emitting element, wherein
the processor is further configured to:
turn off the light emitting element in the readout period, when the light source control value decreases from a first value to a second value in a state where the light emitting element is turned on in the readout period; and
turn on the light emitting element in the readout period, when the light source control value increases from a third value, different from the second value, to a fourth value in a state where the light emitting element is turned off in the readout period, such that the light source control value at which the light emitting element is turned off in a case where the light source control value is in a phase of decreasing and the light source control value at which the light emitting element is turned on in a case where the light source control value is in a phase of increasing are different, wherein
the light emitting element is turned off when the current value in the readout period becomes zero,
the light source control value is set to be over zero even when the light emitting element is turned off, and
the second value of the light source control value indicates a first target value of the light emission amount of the light emitting element in the state where the light emitting element is turned on in the readout period, and the third value of the light source control value indicates a second target value of the light emission amount of the light emitting element in the state where the light emitting element is turned off in the readout period, the second target value being different from the first target value.

2. The medical light source device according to claim 1, wherein the processor is configured to set the current value in the readout period as a minimum rated current value when the light source control value is the first value or the fourth value.

3. The medical light source device according to claim 1, wherein the processor is configured to:
reduce, when the light source control value decreases in a state where the light emitting element is turned on in the readout period, the current value in the readout period while maintaining the light emission amount in the exposure period at a specific light emission amount, and start reducing the light emission amount in the exposure period from the specific light emission amount before turning off the light emitting element in the readout period; and
increase, when the light source control value increases in a state where the light emitting element is turned off in the readout period, the light emission amount in the exposure period, and turn on the light emitting element in the readout period after the light emission amount in the exposure period reaches the specific light emission amount.

4. The medical light source device according to claim 1, wherein the processor is configured to:
turn off, when the light source control value decreases from the first value, smaller than the fourth value, to the second value in a state where the light emitting element is turned on in the readout period, the light emitting element in the readout period; and
turn on, when the light source control value increases from the third value, larger than the second value, to the fourth value in a state where the light emitting element is turned off in the readout period, the light emitting element in the readout period.

5. A medical observation system comprising:
an imaging device including a rolling shutter type image sensor including a plurality of pixels arranged two-dimensionally in units of horizontal lines; and
the medical light source device according to claim 1.

* * * * *